United States Patent [19]

Furutaka et al.

[11] Patent Number: 4,493,800
[45] Date of Patent: Jan. 15, 1985

[54] PROCESS FOR PREPARING A TRIFLUOROMETHYLBENZENE DERIVATIVES

[75] Inventors: Yasuhisa Furutaka, Takatsuki; Sadamu Ishii, Osaka, both of Japan

[73] Assignee: Daikin Kogyo Co., Ltd., Osaka, Japan

[21] Appl. No.: 506,358

[22] Filed: Jun. 21, 1983

[30] Foreign Application Priority Data

Jun. 23, 1982 [JP] Japan .................... 57-108822
Jun. 23, 1982 [JP] Japan .................... 57-108823

[51] Int. Cl.³ ............................ C07C 120/04
[52] U.S. Cl. ................... 260/465 D; 260/465 E; 260/465 F; 260/465 G
[58] Field of Search ........... 260/465 D, 465 E, 465 F, 260/465 G

[56] References Cited

U.S. PATENT DOCUMENTS 4,285,883 8/1981 Yoshikawa ............... 260/465 G

Primary Examiner—Dolph H. Torrence
Attorney, Agent, or Firm—Birch, Stewart, Kolasch & Birch

[57] ABSTRACT

A process for preparing a trifluoromethylbenzonitrile derivative of the formula:

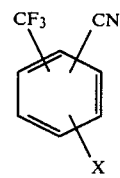

wherein X is hydrogen, lower alkyl, halogenated lower alkyl, lower alkoxy, nitro, hydroxyl, amino, cyano, carboxyl or sulfon which comprises reacting trifluoromethylhalogenobenzene of the formula:

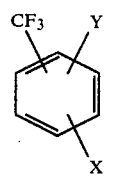

wherein X is as defined above, and Y is halogen with copper (I) cyanide in a solvent selected from the group consisting of hexamethylphosphoric triamide, N-methylpyrrolidone and a mixture thereof in the presence of a catalyst selected from the group consisting of (A) bromine, (B) iodine, (C) a combination of bromine or iodine and metallic copper and (D) copper (II) bromide, by which process the compound (I) is prepared in a good yield, and by-products are produced in a lower yield than the conventional processes.

4 Claims, No Drawings

PROCESS FOR PREPARING TRIFLUOROMETHYLBENZENE DERIVATIVES

This invention relates to a process for preparing trifluoromethylbenzene derivatives. More particularly, it relates to a process for preparing trifluoromethylbenzene derivatives comprising reacting trifluoromethylhalogenobenzene or a derivative thereof with copper(I) cyanide.

Generally, aromatic halogenocompounds are much less reactive than aliphatic halogenocompounds and do not undergo nucleophilic substitution of the $S_NAr$ type if they are not activated by a suitable electron withdrawing group. It is well recognized that a trifluoromethyl group is an electron withdrawing group which exhibits $-I$ and $-E$ effects due to the electronegativity of fluorine atoms and the negative hyperconjugation, but activates the aromatic ring against the nucleophilic attack to a less extent. When a cyano group is to be introduced in trifluoromethylhalogenobenzene by the use of an alkali metal cyanide, the cyanide reacts more easily with the trifluoromethyl group than with the benzene ring, so that it is difficult to obtain desired benzonitrile derivatives.

The Rosenmund-von Braun reaction is a well known reaction to prepare an aromatic nitrile from a corresponding aromatic halogenocompound. In the reaction, an aromatic bromocompound and copper(I) cyanide are reacted at a temperature of 250° to 260° C. to substitute the bromine atom with the cyano group. However, the reaction requires severe reaction conditions and is accompanied with side reactions. Recently, it has been proposed to react the aromatic halogenocompound with copper(I) cyanide in the presence of palladium salts or palladium-phosphine complexes. This reaction is, however, not suitable for commercial production.

As a result of an extensive study to provide a simple and effective process for preparing trifluoromethylbenzonitrile or a derivative thereof from corresponding trifluoromethylhalogenobenzene or its derivatives, which process is not accompanied with the side reactions, it has now been found that when trifluoromethylhalogenobenzene is reacted with copper(I) cyanide in a certain specific solvent in the presence of a catalyst selected from the group consisting of (A) bromine, (B) iodine, (C) a combination of bromine or iodine and metallic copper and (D) copper(II) bromide, the cyano group is effectively introduced in the aromatic ring.

According to the present invention, there is provided a process for preparing trifluoromethylbenzene derivatives or a derivative thereof of the formula:

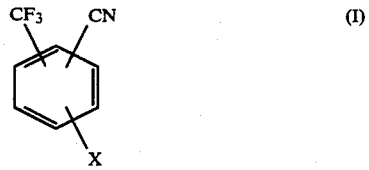

(I)

wherein X is hydrogen, lower alkyl, halogenated lower alkyl, lower alkoxy, nitro, hydroxyl, amino, cyano, carboxyl or sulfon, which comprises reacting trifluoromethylhalogenobenzene or a derivative thereof of the formula:

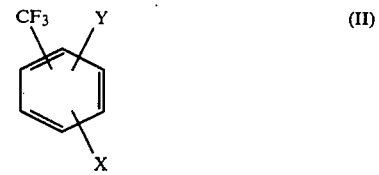

(II)

wherein X is as defined above, and Y is halogen with copper(I) cyanide in a solvent selected from the group consisting of hexamethylphosphoric triamide, N-methylpyrrolidone and a mixture thereof in the presence of a catalyst selected from the group consisting of (A) bromine, (B) iodine, (C) a combination of bromine or iodine and metallic copper and (D) copper(II) bromide.

In the formulas, lower alkyl means $C_1$–$C_5$ alkyl, and lower alkoxy means $C_1$–$C_5$ alkoxy.

Specific examples of trifluoromethylhalogenobenzene derivatives (II) to be used as a starting material are o-, m- and p-chlorobenzotrifluoride, o-, m- and p-bromobenzotrifluoride, o-, m- and p-iodobenzotrifluoride, 2-chloro-5-nitrobenzotrifluoride, 2-nitro-5-chlorobenzotrifluoride, 3-nitro-4-chlorobenzotrifluoride, 2-nitro-5-bromobenzotrifluoride, 2-chloro-5-aminobenzotrifluoride, 3-amino-4-chlorobenzotrifluoride, 2-amino-5-chlorobenzotrifluoride, 2-bromo-5-aminobenzotrifluoride, 3-amino-4-bromobenzotrifluoride, 2-amino-5-bromobenzotrifluoride, 2-chloro-5-carboxybenzotrifluoride, 3-carboxy-4-chlorobenzotrifluoride, 2-carboxy-5-chlorobenzotrifluoride, 2-chloro-5-cyanobenzotrifluoride, 2-cyano-5-chlorobenzotrifluoride, 3-cyano-4-chlorobenzotrifluoride, 3-bromo-5-trifluromethylbenzotrifluoride, 2,3-difluorobenzotrifluoride, 2,4-dichlorobenzotrifluoride, 2,5-dichlorobenzotrifluoride, 3,4-dichlorobenzotrifluoride, 3,5-dichlorobenzotrifluoride, 2-chloro-4-methylbenzotrifluoride, 4-methoxybenzotrifluoride, 3-dichloromethyl-5-chlorobenzotrifluoride, etc.

The molar ratio of copper (I) cyanide and trifluoromethylhalogenobenzene derivatives (II) in the invention is from 1:10 to 10:1, preferably from 1:3 to 3:1. In addition to copper(I) cyanide, alkali metal cyanide (e.g. potassium cyanide, sodium cyanide, etc.) may be added to the reaction system.

The catalyst may be used in a range between 0.02 and 10 moles, preferably between 0.2 and 5 moles per 1 mole of trifluoromethylhalogenobenzene (I).

As the solvent, an aprotic polar solvent such as hexamethylphosphoric triamide (hereinafter referred to as "HMPA"), N-methylpyrrolidone (hereinafter referred to as "NMP") and a mixture thereof is used. Further, the solvent may be mixed with at least one other polar solvent, examples of which are dimethylformamide, dimethylacetamide, sulfolane, glymes, etc. When the starting material has a halogen atom at a position where the strong electron withdrawing group (e.g. a nitro group) and the trifluoromethyl group act in a synergistic manner, NMP may be preferred.

The reaction of the invention may carried out at a temperature of from 100° to 250° C., preferably from 150° to 210° C., particularly from 190° to 200° C. under an atmospheric pressure for 1 to 10 hours.

The thus prepared trifluoromethylbenzonitrile derivative (I) may be subjected to acidic or basic hydrolysis to give benzoic acid or its derivatives or phthalic acid or its derivatives.

The trifluoromethylbenzonitrile (I) is useful as a bacteriocide and/or a herbicide.

The present invention will hereinafter explained further in detail by following Examples.

EXAMPLE 1

In a 200 ml flask, HMPA (50 ml), copper(I) cyanide (14.3 g, 160 mmole) and iodine (10 g, 40 mml) were charged, and then p-chlorobenzotrifluoride (7.22 g, 40 mmole) was added. The mixture was reacted at 210° C. with sirring for 6 hours. The reaction mixture was analyzed by gas chromatography (column: SE-30). The yield of p-trifluoromethylbenzonitrile was 70%.

EXAMPLES 2 to 6

In the same manner as in Example 1 but using a starting material, a catalyst and a solvent as shown in Table 1 and carrying the reaction under predetermined reaction conditions, p-trifluoromethylbenzonitrile was prepared. The yields are shown in Table 1.

TABLE 1

| Example | p-Chlorobenzo-trifluoride (g) | Copper cyanide (g) | Solvent (ml) | Bromide or iodide (g) | Copper powder (g) | Temp. (°C.) | Time (hrs) | Yield (%) |
|---|---|---|---|---|---|---|---|---|
| 2 | 7.22 | 14.3 | HMPA (50) | Br$_2$ (6.4) | — | 210 | 7 | 70 |
| 3 | 7.60 | 14.3 | NMP (50) | Br$_2$ (6.4) | — | 190 −195 | 9 | 80 |
| 4 | 7.22 | 3.6 | NMP (50) | Br$_2$ (6.4) | 5.1 | 195 | 9 | 95 |
| 5 | 7.22 | 14.3 | NMP (25) Sulfolane (25) | Br$_2$ (6.4) | — | 200 −207 | 8 | 95 |
| 6 | 7.22 | 7.2 | NMP (25) Sulfolane (25) | Br$_2$ (6.4) | 5.1 | 200 −207 | 7 | 95 |

EXAMPLE 7

In a 200 ml flask, p-chlorobenzotrifluoride (7.80 g, 43 mmole), copper(I) cyanide (7.17 g, 80 mmole), copper(II) bromide (10 g, 45 mmole) and HMPA (50 ml) were charged and reacted at 210° C. with sirring for 9 hours. The reaction mixture was analyzed by gas chromatography. The yield of p-trifluoromethylbenzonitrile was 99%.

EXAMPLES 8 TO 10 AND COMPARATIVE EXAMPLES 1 TO 4

In the same manner as in Example 7 but using a staring material, a copper(II) salt and a solvent as shown in Table 2 and carrying the reaction under predetermined reaction conditions, p-trifluoromethylbenzonitrile was prepared. The yields are shown in Table 2.

TABLE 2

| | p-Chlorobenzo-trifluoride (g) | Copper cyanide (g) | Solvent (ml) | Copper salt (g) | Temp. (°C.) | Time (hrs) | Yield (%) |
|---|---|---|---|---|---|---|---|
| Example 8 | 7.22 | 7.17 | NMP (50) | CuBr$_2$ (10) | 195 | 9 | 80 |
| Example 9 | 7.80 | 7.17 | NMP (25) Sulfolane (25) | CuBr$_2$ (4.5) | 200 | 9 | 73 |
| Example 10 | 7.80 | 7.17 | NMP (25) Sulfolane (25) | CuBr$_2$ (10) | 200 | 9 | 90 |
| Comparative Example 1 | 7.22 | 7.17 | NMP (50) | CuBr (13) | 195 | 9 | 39 |
| Comparative Example 2 | 7.80 | 7.17 | HMPA (50) | CuSO$_4$ (15) | 210 | 9 | 0 |
| Comparative Example 3 | 7.80 | 7.17 | NMP (50) | CuSO$_4$ (15) | 195 | 9 | 0 |
| Comparative Example 4 | 7.80 | 7.17 | NMP (50) | Cu(NO$_3$)$_2$ (18.7) | 195 | 9 | 0 |

What is claimed is:

1. A process for preparing a trifluoromethylbenzonitrile derivative of the formula:

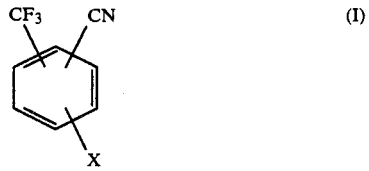

(I)

wherein X is hydrogen, lower alkyl, halogenated lower alkyl, lower alkoxy, nitro, hydroxyl, amino, cyano, carboxyl or sulfon, which comprises reacting a trifluoromethylhalogenobenzene derivative of the formula:

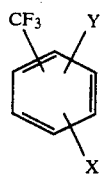 (II)

wherein X is as defined above, and Y is halogen with copper(I) cyanide in a solvent selected from the group consisting of hexamethylphosphoric triamide, N-methylpyrrolidone and mixture thereof in the presence of a catalyst selected from the group consisting of (A) bromine, (B) iodine, (C) a combination of bromine or iodine and metallic copper and (D) copper(II) bromide.

2. The process according to claim 1, wherein the molar ratio of copper(I) cyanide and triflurormethylhalogenobenzene derivative (II) is from 1:10 to 10:1.

3. The process according to claim 1, wherein the catalyst is used in the range between 0.02 and 10 moles per 1 mole of trifluoromethylhalogenobenzene derivative.

4. The process according to claim 1, wherein the reaction temperature is from 100° to 250° C.

5. The process according to claim 1, wherein the solvent is N-methylpyrrolidone.

6. The process according to claim 4, wherein the reaction temperature is from 150° to 210° C.

* * * * *